(12) United States Patent
Suzuki et al.

(10) Patent No.: US 6,963,397 B2
(45) Date of Patent: Nov. 8, 2005

(54) FLUOROMETRY AND FLUOROMETRIC DEVICE AND SUBSTRATE SUITABLE THEREFOR

(75) Inventors: Tomohiro Suzuki, Sagamihara (JP); Tadashi Okamoto, Yokohama (JP); Kazuhiro Matsumoto, Utsunomiya (JP); Nobuko Yamamoto, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 70 days.

(21) Appl. No.: 09/764,049

(22) Filed: Jan. 19, 2001

(65) Prior Publication Data

US 2001/0055114 A1 Dec. 27, 2001

(51) Int. Cl.⁷ .............................................. G01N 21/64
(52) U.S. Cl. ...................... 356/317; 250/458.1; 356/244
(58) Field of Search ............................... 356/317, 318, 356/417; 250/458.1, 459.1, 461.1, 461.2; 436/172

(56) References Cited

U.S. PATENT DOCUMENTS

| | | | | |
|---|---|---|---|---|
| 4,778,763 A | * | 10/1988 | Makiguchi et al. ............ | 436/47 |
| 5,528,050 A | * | 6/1996 | Miller et al. .............. | 250/458.1 |
| 6,071,702 A | * | 6/2000 | Yamamoto et al. ............ | 435/6 |
| 6,399,952 B1 | * | 6/2002 | Maher et al. ............ | 250/458.1 |

FOREIGN PATENT DOCUMENTS

| | | | |
|---|---|---|---|
| JP | 2000-321206 | * 11/2000 | |
| WO | WO 00/68668 | * 11/2000 | .......... G01N/21/64 |

OTHER PUBLICATIONS

U.S. Appl. No. 09/764,419, filed Jan. 19, 2001, Suzuki et al.

* cited by examiner

Primary Examiner—F. L. Evans
(74) Attorney, Agent, or Firm—Fitzpatrick, Cella, Harper and Scinto

(57) ABSTRACT

To provide a method of efficiently removing excitation light in a device for measuring fluorescence emitted from samples on a measuring surface of a substrate while illuminating the samples with excitation light.

The method is a fluorometry characterized in that an excitation light illumination portion where the samples are illuminated with the excitation light and a light detecting portion where measurements are made of the fluorescence are placed in such a manner as to make it possible to prevent the excitation light from approaching the light detecting portion, and measurements of the fluorescence emitted from the samples on the measuring surface of the substrate are made in such a manner as to relatively move the samples from the excitation light illumination portion to the light detecting portion after illuminating the same with the excitation light.

17 Claims, 3 Drawing Sheets

FLUOROMETRY AND FLUOROMETRIC DEVICE AND SUBSTRATE SUITABLE THEREFOR

BACKGROUND OF THE INVENTION

1. Field of the Invention

The present invention relates to a method and a device for measuring fluorescence of samples, in particular, to method for measuring fluorescence of samples on a surface of a disk-shaped substrate. The present invention also relates to a substrate suitable for the fluorometry.

2. Related Background Art

The use of fluorescence is indispensable for the measurements for a very slight amount of substances such as samples taken from organisms. There are some other means of measuring for a very slight amount of substances, such as radioisotope and nuclear magnetic resonance, however, the fluorometry has the widest applications in terms of sensitivity, wide variety of labeling substances applicable, easiness of handling, usability for general-purpose, improvement in light detection sensitivity.

The fluorometry is applied not only to staining cells and tissues, which is for making the same visible, but also to quantifying substances since it is capable of making measurements quantitatively. Particularly in the detection of a very slight amount of substances, it can form a detection system of high sensitivity and specificity in combination with specific reactions, such as antigen-antibody reaction with biomolecules and hybridization with DNAs having specific base sequences.

One of the requirements in the measurement of fluorescence is the separation of excitation light. This means that fluorescence alone has to be measured by making some devices for preventing excitation light from approaching the light detecting portion.

For example, in an ordinary erection type fluorescence microscope, a dichroic mirror and a filter are mounted thereon so as to prevent the excitation light reflected or scattered by samples from approaching the light detecting portion. In a device for measuring the lifetime of fluorescence, the excitation light is prevented from approaching the light detecting portion by the use of a pulse light emission source at the time of measuring fluorescence. And in a spectrofluorometer, the excitation light is made to approach the light detecting portion as rarely as possible by allowing the excitation light and the optical axis of the light detecting portion to be perpendicular to each other.

The use of the above methods enables performing the measurement of fluorescence while preventing the majority of the excitation light from approaching the light detecting portion. However, it goes without saying that even the above devices cannot prevent 100% of the excitation light from approaching the light detecting portion and, in actuality, some of the excitation light leaks to the light detecting portion, though it is very slight compared with the intensity of the excitation light.

SUMMARY OF THE INVENTION

When the amount of the samples is relatively large and fluorescence is easy to observe, or when the fluorescent substance contains a lot of fluorescent dye with a sufficient intensity, the approach of a slight amount of excitation light to the light detecting portion (leaky light) is not a problem and does not affect the measurement of fluorescence. This is because the intensity of the fluorescence emitted is overwhelmingly high compared with the leaky light and the leaky light does not affect the situation as a whole.

However, when measuring a slight amount of faint fluorescence, the leaky light can sometimes affect the measurement seriously. According to the situation, the amount of the leaky light may be larger than that of the fluorescence emitted.

There are cases where a band-pass filter is inserted in front of the light detecting portion, as the preventive measures; however, since the fluorescence subjected to measurement is faint, the insertion of such a filter sometimes result in insufficient amount of fluorescence subjected to measurement.

Further in many fluorochromes, their fluorescent wavelength is often close to that of the excitation light, and there may be cases where a part of the short wavelength region of the fluorescence and a part of the long wavelength region of the excitation light overlap each other; thus, the above two types of light are hard to separate clearly in principle.

In recent years, the sensitivity of cameras has been substantially increased and measurement of light even at a photon counting level has been made possible. Therefore, if the excitation light can be removed more efficiently and the measurement of faint fluorescence is made possible, the merit of the application of fluorometry is more increased.

Accordingly the object of the present invention is to overcome the above-described problems, in other words, to remove the excitation light from the light detecting portion more effectively.

Specifically, according to one aspect of the present invention, there is provided a fluorometry for measuring fluorescence emitted from samples on a measuring surface of a substrate by illuminating the samples with excitation light, characterized in that an excitation light illumination portion and a light detecting portion are placed in such a manner as to make it possible to prevent the excitation light from approaching the light detecting portion where measurement of the fluorescence is performed, the fluorescence emitted from the samples is measured by relatively moving the samples on the measuring surface of the substrate from the excitation light illumination portion to the light detecting portion after illuminating the samples with the excitation light.

Preferably, the method of the present invention is characterized in that a circular orbit is formed on the measuring surface of the substrate by relatively moving the samples.

Preferably, the method of the present invention is characterized in that the circular orbit is formed while forming a rotational plane of the measuring surface by rotating the substrate around the axis perpendicular to the measuring surface thereof and the samples are moved from the excitation light illumination portion to the light detecting portion relative to the rotational plane of the measuring surface.

Or preferably, the method of the present invention is characterized in that the circular orbit of the measuring area is formed by allowing the excitation, light illumination portion and the light detecting portion to perform a rotational movement.

Preferably, the method of the present invention is characterized in that the samples are liquid filled in cells formed on the substrate or are substances fixed on, adsorbed onto, or trapped in the substrate, and that the samples are fixed in the probes arranged on the substrate.

Preferably, the method of the present invention is characterized in that the probes and the sample are DNA, protein or peptide nucleic acid (PNA).

Preferably, the method of the present invention is characterized in that the spacing between the excitation light illumination position and the light detecting portion is variable or the moving speed of the sample is variable, and that the period from the illumination of excitation light to the detection of fluorescence is properly adjustable by varying the moving speed.

Preferably, the method of the present invention is characterized in that the samples on the measuring surface of the substrate are arranged on more than one circles or on the arcs thereof which are concentric with the central axis of the substrate and are different in radius from each other, and that the samples at the same distance from the central axis have the same or similar attributes and form a group which can be discriminated from the other groups of samples.

According to another aspect of the present invention there is provided a substrate having samples, which are subjected to fluorescence measurement, on its measuring surface, characterized in that the samples are arranged on more than one circles or the arcs thereof which are concentric with the central axis of the substrate and are different in radius from each other, and that the samples at the same distance from the central axis have the same or similar attributes and form a group which can be discriminated from the other groups of samples.

According to further aspect of the present invention there is provided a fluorometric device which includes an excitation light illumination portion where samples on the measuring surface of a substrate are illuminated with excitation light and a light detecting portion where the measurement of the fluorescence emitted from the samples is performed, characterized in that the excitation light illumination portion and the light detecting portion are placed in such a manner as to make it possible to prevent the excitation light from approaching the light detecting portion, a means is provided for relatively moving the samples on the measuring surface of the substrate from the excitation light illumination portion to the light detecting portion, the means for relatively moving the samples being preferably such that it moves the substrate having the samples on the measuring surface relative to the excitation light illumination portion and the light detecting portion while allowing the same to form a circular orbit.

DETAILED DESCRIPTION OF THE PREFERRED EMBODIMENTS

Figure 1:
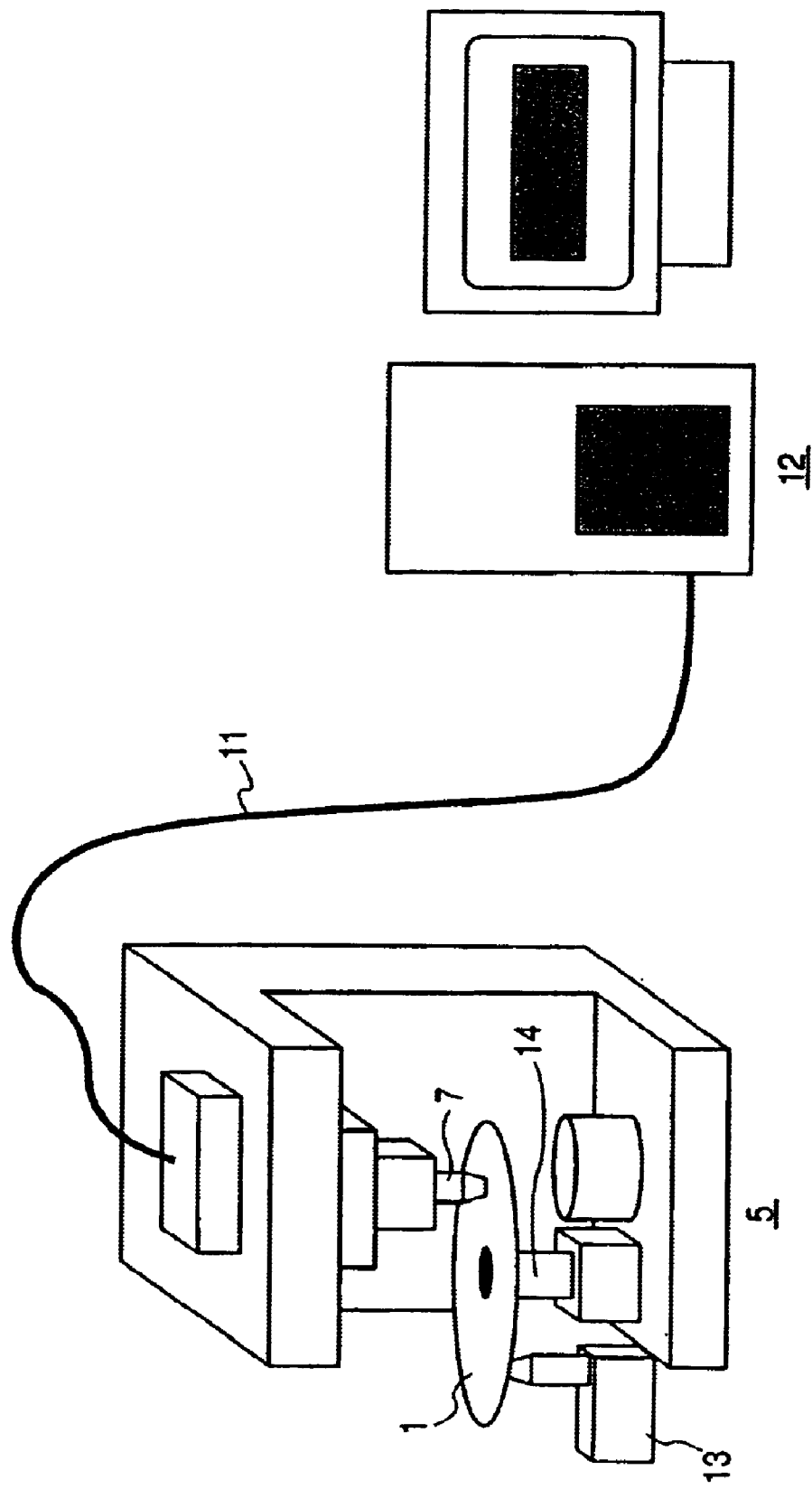
FIG. 1 is a view of a fluorometric device in accordance with the present invention.

The fluorometry and fluorometric device in accordance with the present invention are characterized in that the light detecting portion is placed in such a position that excitation light does not enter it and a mechanism is provided which prevents the excitation light from approaching the light detecting portion by moving samples from the excitation light illumination portion to the light detecting portion after illuminating the samples with the excitation light.

The optical axis of the excitation light and that of the light detecting portion are completely different from each other, thereby the excitation light can be inhibited from approaching the light detecting portion in principle. However, in view of the influence of excitation light propagation and scattering in the glass due to its reflection within the substrate, the inhibition of the excitation light from approaching the light detecting portion can be ensured by taking the following measures:

a) using black glass for the substrate instead of glass;

b) covering both the excitation light illumination portion and the light detecting portion so as to block off the scattered light spatially; and c) increasing the flatness of the substrate surface and illuminating the substrate with the excitation light perpendicular thereto so as to decrease the light scattering on the surface of the substrate.

It goes without saying that desirably the movement of the sample from the excitation light illumination portion to the light detecting portion is performed within the period of the fluorescence lifetime of, for example, fluorochrome contained in the samples.

The dyes excited by the illumination with the excitation light emit fluorescence; however, the intensity of the fluorescence decreases with time. Therefore, it is necessary to move the samples to the light detecting portion while they are emitting a measurable amount of fluorescence after completion of the excitation light illumination.

There are various methods of moving samples. When samples are fixed on the surface of a disk-shaped substrate or they are liquid filled in cells formed on a disk, they can be moved easily by rotating the disk.

For example, one spot of the rotating disk is illuminated with excitation light, and when the light-illuminated measuring spot passes through, with the rotation of the disk, a place where the light detecting portion is placed, a measurement is performed. The light detecting portion is placed in such a position that the light-illuminated measuring spot can pass through it while the samples are emitting fluorescence. If the disk continues to be rotated, the samples are again excited at the same excitation light illumination spot after the first measurement and another measurement can be made; thus, if necessary, multiple measurements can be made and their results can be integrated.

When the samples are hard to rotate, they may be moved linearly in a fixed direction. In such a case, the excitation light illumination portion and the light detecting portion are properly spaced and the samples having been illuminated with the excitation light are moved in such a manner as to reach the light detecting portion while they are emitting fluorescence, just like the cases where the samples are rotated.

In many cases, it is easier to move the samples than to move both the excitation light illumination portion and the light detecting portion, in terms of the device's structure; however, when the samples are hard to move, the excitation light illumination portion and the light detecting portion may be moved relative to the samples.

More than one excitation light illumination portions and light detecting portions can be placed. For example, the samples can be subjected to measurements at more than one-different spots under different conditions after being illuminated with excitation light at one spot. Alternatively, in view of the efficiency in measuring time, measurements can be made at more than one different spots in parallel.

The period of time from the excitation light illumination to the samples' passing through the light detecting portion depends on the spacing between the excitation light illumination portion and the light detecting portion as well as the moving speed of the samples. Because the lifetime of fluorescence varies depending on the kinds of, for example, dyes emitting fluorescence, the device is desirably such that the spacing between the excitation light illumination portion and the light detecting portion as well as the moving speed of the samples are variable.

The fluorometry in accordance with the present invention is applicable to the substance detection using a solid-phase substrate, to which attention has been being paid in recent years. When making measurements for samples using fluorescence after reacting the samples with a substrate, in particular, a solid-phase substrate on which probes such as DNA and proteins are provided, the measurements have to be made for a very slight amount of fluorescent substance on the substrate. And in order to make high-sensitivity measurements, efficient removal of excitation light is a key factor. The fluorometry in accordance with the present invention enables the improvement in removal of excitation light.

When utilizing the fluorometric device in accordance with the present invention for the micro-measurements using the substrate described above, measurements with more than one types of probes are made possibly only by allowing the light detecting portion on the substrate to take the form of concentric circulars, that is, by allowing each of the probes to have a pattern of a circle with its center at the rotational center of the substrate and using a substrate on which the probes are arranged in the form of concentric circles with different radii. In this case, measurements are made while adjusting the light detecting portion (usually objective lens) to the rotating substrate, and measurements for the sample corresponding to more than one probes can be performed by varying the distance from the rotational center to each probe.

EXAMPLES

Example 1

(1) Preparation of Substrate

A silica glass substrate 30 mm in diameter and 0.5 mm in thickness was prepared. In order to allow the substrate to rotate, the circular portion of the substrate within 10 mm from its center was designed in such a manner as to make it possible to transmit the rotational drive thereto.

The silica glass substrate was water-washed lightly, subjected to ultrasonic cleaning for 20 minutes while being immersed in an exclusive substrate cleaning solution, and left stand one whole day and night. Then the substrate was taken from the cleaning solution, washed with water and deionized water so as to take the cleaning solution away therefrom, and immersed in 1M NaOH aqueous solution preheated to 60° C. for 20 minutes. The substrate was taken from the NaOH aqueous solution, again washed with water and deionized water so as to take the NaOH aqueous solution away therefrom, and subjected to ultrasonic cleaning in deionized water for 20 minutes.

Then the substrate was immersed in a silane coupling agent (manufactured by Shin-Etsu Chemical Co., Ltd., brand name: KBM 603), which was previously dissolved in water to be 1% aqueous solution and subjected to hydrolysis for about one hour, for one hour. The substrate was washed lightly with deionized water, dried by blowing the water droplets remaining on the surface away with nitrogen gas, and baked in an oven at 120° C. for 2 hours. Amino groups were introduced to the glass surface by attaching the silane coupling agent to the same.

(2) Dye Attachment

Then 2 ml of a solution of eosin-5-isothiocyanate, a protein labeling dye manufactured by Funakoshi Co., Ltd., in 1M NaCl/50 mM sodium phosphate buffer solution (pH 7.0) (50 $\mu$M concentration) was prepared, and the solution was reacted with the substrate for 10 hours in a hybridization package. After the completion of the reaction, the substrate was washed with 1M NaCl/50 mM sodium phosphate buffer solution (pH 7.0) to take the unreacted eosin-5-isothiocyanate away therefrom, and a substrate 1 with eosin attached thereto was obtained.

(3) Device Construction

Figure 2:
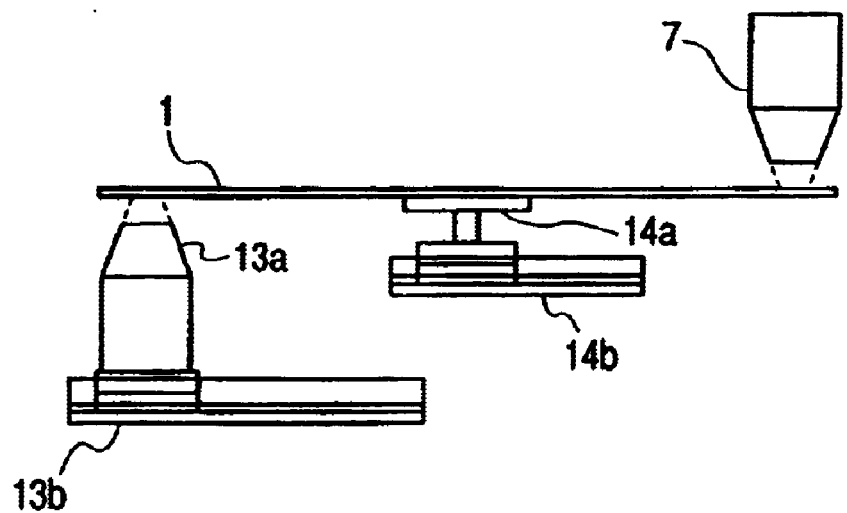
FIG. 2 is an enlarged view of the stage portion.
Figure 3:
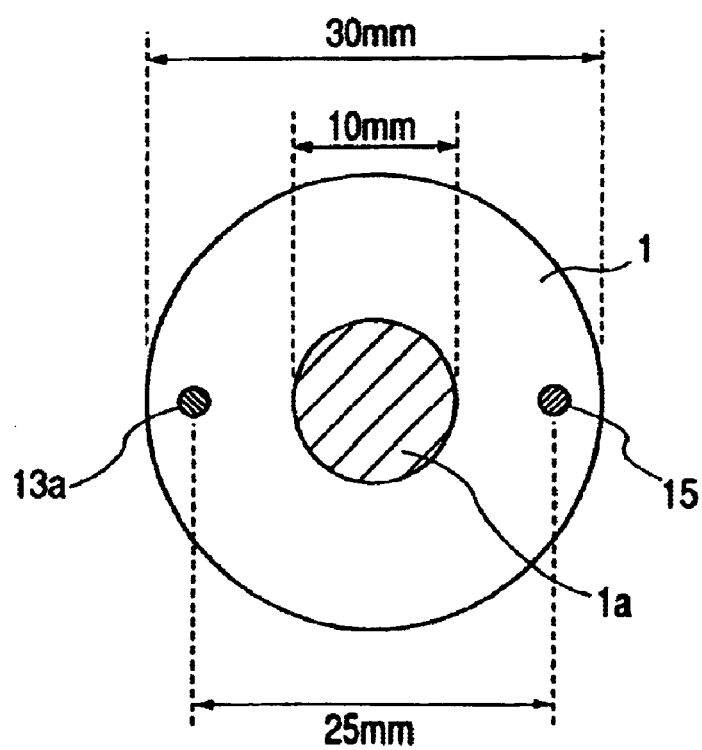
FIG. 3 is a view showing the positional relation between the excitation light illumination portion and the light detecting portion.

A measuring device shown in FIG. 1 was prepared by remodeling the stage portion of a fluorescence microscope manufactured by Nikon Corporation. FIG. 2 is an enlarged view of the stage portion and its vicinities. Reference numeral 13 denotes an excitation light illumination device; 13a, an excitation light illumination portion; and 13b, a stage for moving the excitation light illumination portion 13a. The excitation light illumination portion 13a and an objective lens 7 of the fluorescence microscope, as a light detecting portion 15, are placed on the opposite sides relative to the central axis of a the disk, and on the central portion 1a of the disk a rotational drive device 14 was placed for rotating the substrate. Reference numeral 14a denotes a rotating portion; and 14b, a stage for moving the rotating portion 14a. Although the distance from the central axis to the excitation light illumination portion and that from the central axis to the light detecting portion 15 were variable, both the portions were fixed on the opposite sides relative to the central axis at a distance 12.5 mm from the central axis. In other words, both the excitation light illumination portion and the light detecting portion 15 were placed in such a manner that, when the disk was turned 180°, the portion illuminated with excitation light was moved to the light detecting portion 15 (see FIG. 3).

The measuring device was designed in such a manner that the light obtained from the objective lens 7, as the light detecting portion 15, was sent to a fluorometric device 12 via an optical fiber 11 extending from the microscope 5, so as to be analyzed there. This fluorometric device 12 is capable of integrating data, and when the fluorescence obtained is very faint, its sensitivity can be increased by integrating data.

(4) Substrate Measurement

Figure 4:
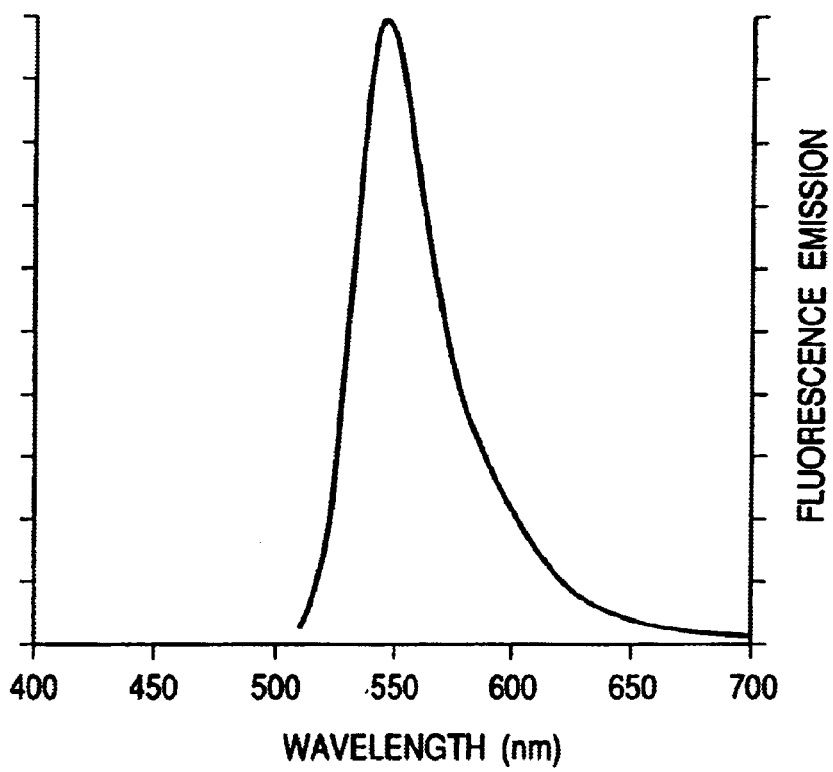
FIG. 4 is a graphical representation of the fluorescent spectrum of a sample obtained by a fluorometric device.

The previously prepared substrate 1 with eosin attached thereto was fixed on the remodeled stage. The rotation speed of the disk was set at 30000 rpm and the excitation light at 522 nm.

a Measurements were made while illuminating the samples with excitation light and continued for 10 seconds until sufficient sensitivity was obtained, and the fluorescence detected from the substrate was integrated. As a result, the spectrum shown FIG. 4 was obtained.

There was no appreciable peak around the wavelength of 522 nm, which was the wavelength of the excitation light, and the fluorescence derived solely from eosin was measured.

Thus, the fluorometry in accordance with the present invention enabled the measurement of the fluorescence of the samples without excitation light.

Example 2

(1) Preparation of Substrate

A silica glass substrate 30 mm in diameter and 1 mm in thickness was prepared. In order to allow the substrate to rotate, the circular portion of the substrate within 10 mm from its center was designed in such a manner as to make it possible to transmit the rotational drive thereto.

The silica glass substrate was water-washed lightly, subjected to ultrasonic cleaning for 20 minutes while being immersed in an exclusive substrate cleaning solution, and left stand one whole day and night. Then the substrate was taken from the cleaning solution, washed with water and deionized water so as to take the cleaning solution away therefrom, and immersed in 1 M NaOH aqueous solution preheated to 60° C. for 20 minutes. The substrate was taken from the NaOH aqueous solution, again washed with water and deionized water sodas to take the NaOH aqueous solution away therefrom, and subjected to ultrasonic cleaning in deionized water for 20 minutes.

Then the substrate was immersed in a silane coupling agent (manufactured by Shin-Etsu, Chemical Co., Ltd., brand name: KBM 603), which was previously dissolved in water at a final concentration of 1% and subjected to hydrolysis for about one hour, for one hour. The substrate was washed lightly with deionized water, dried by blowing the water droplets remaining on the surface away with nitrogen gas, and baked in an oven at 120° C. for 2 hours. Amino groups were introduced to the glass surface by attaching the silane coupling agent to the same.

Then a crosslinking agent, EMCS (N-(6-Maleimidocaproyloxy)succinimide), manufactured by Dojindo Laboratories was dissolved in a mixed solvent (ethanol:DMSO=1:1) in the proportion of 3 mg to 10 ml. The substrate having been baked previously was immersed in the obtained EMCS solution and left for 2 hours. After taking the substrate from the EMCS solution and washing the same lightly with the same mixed solvent as above, the droplets remaining on the surface of the substrate was subjected to substitution into ethanol, and the substrate was dried by blowing the droplets away with nitrogen gas. Thus a substrate (EMCS-treated substrate) was obtained the entire surface (the surface of both sides) of which EMCS was attached to. EMCS contains a succinimide group and a maleimido group; and since the succinimide group binds to the amino group on the surface of the substrate, the surface of the substrate had the maleimido group having been introduced thereon.

(2) DNA Attachment

Modified 18-mer DNA (probe) with a thiol group (SH group) attached to one terminal thereof was synthesized by BEX at the request of the applicants of the present invention. The SH group was attached to 5' terminal and the DNA base sequence was as follows:

$^{5'}$HS-ACTGGCCGTCGTTTTACA$^{3'}$ (SEQ ID No. 1)

The above DNA was dissolved in water at a final concentration of 30 µM. Two ml of the obtained DNA aqueous solution was sealed into a hybridization package together with the previously prepared EMCS-treated substrate, so as to subject them to hybridization reaction for 2 hours. After the completion of the reaction, the substrate was washed with 1M NaCl/50 mM sodium phosphate buffer solution (pH 7.0) so as to completely wash the DNA solution away from the glass surface. Then the substrate was immersed in 2% bovine serum albumin aqueous solution, left for 2 hours, and subjected to blocking reaction. After the blocking reaction, the substrate was again washed with 1M NaCl/50 mM sodium phosphate buffer solution (pH 7.0), so as to obtain the substrate to which DNA was attached.

(3) Synthesis of EOSIN-Labeled DNA

Amino-linked 18-mer DNA having a sequence complementary to that of the DNA attached to the substrate was synthesized by BEX at the request of the applicants of the present invention. As the amino group, used was a commonly used 5'-terminal-hexamethylene type amino linker.

5'-terminal-eosin-labeled DNA was obtained by reacting the amino-linked DNA with eosin-5-isothiocyanate, a protein-labeling dye manufactured by Funakoshi Co., Ltd. Labeling reaction was carried out by conventional procedure.

(4) Hybridization

Eosin-labeled DNA was dissolved in 1M NaCl/50 mM sodium phosphate buffer solution (pH 7.0) at a final concentration of 1 µM, 2 ml of the obtained DNA solution was sealed into a hybridization package together with the previously prepared substrate, so as to subject them to hybridization reaction for 3 hours.

After the reaction, the substrate was washed with 1M NaCl/50 mM sodium phosphate buffer solution (pH 7.0), so as to obtain the substrate 1, as the subject of measurements.

(5) Substrate Measurement

Measurements were made for the obtained substrate 1 with the measuring device used in the example 1. The rotation speed of the disk was set at 30000 rpm and the excitation light at 522 nm, like in the example 1.

Measurements were made while illuminating the samples with excitation light and continued for 10 seconds until sufficient sensitivity was obtained, and the fluorescence detected from the substrate was integrated. As a result, the same spectrum as obtained in the example 1 (shown FIG. 4) was obtained.

Like in the example 1, there was no appreciable peak around the wavelength of 522 nm, and the fluorescence derived solely from eosin was measured. Thus, the fluorometry in accordance with the present invention enabled the measurement of the fluorescence of the samples without excitation light.

Example 3

(1) Preparation of Substrate

An EMCS-treated substrate, the entire surface of which EMCS was attached to, 30 mm in diameter was obtained in the same manner as in the example 2 (1).

(2) DNA Attachment

Modified 18-mer DNAs (probes) with a thiol group (SH group) attached to one terminal thereof were synthesized by BEX at the request of the applicants of this invention. The SH group was attached to 5' a terminal and the DNA base sequence was as follows:

No. 1: $^{5'}$HS-ACTGGCCGTCGTTTTACA$^{3'}$ (SEQ ID No. 1)
No. 2: $^{5'}$HS-ACTGGCCGTTGTTTTACA$^{3'}$ (SEQ ID No. 2)
No. 3: $^{5'}$HS-ACTGGCCGCTTTTTACA$^{3'}$ (SEQ ID No. 3)
No. 4: $^{5'}$HS-ACTGGCATCTTGTTTACA$^{3'}$ (SEQ ID No. 4)

Figure 5:
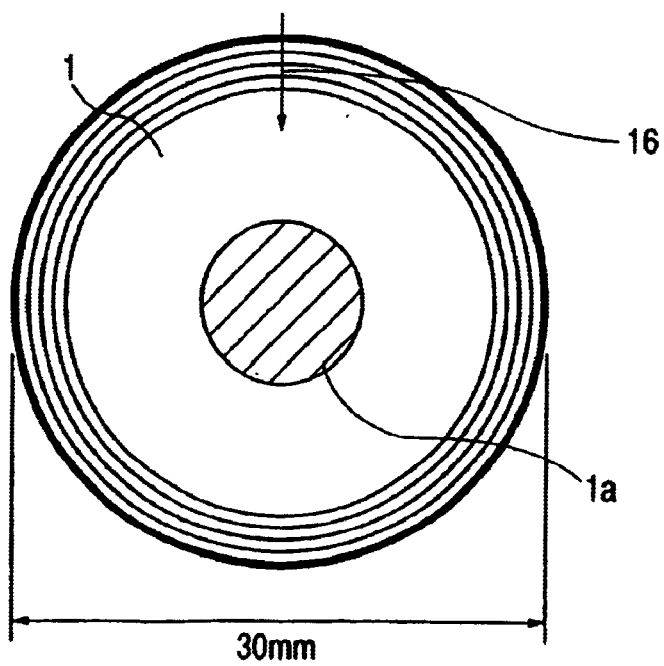
FIG. 5 is a view of a substrate on which 4 types of probes are arranged in such a manner as to form concentric circles.

The above DNAs were dissolved in SG Clear (aqueous solution containing 7.5% of glycerol, 7.5% of urea, 7.5% of thiodiglycol and 1% of acetylenol EH), which is a solvent for use in thermal jet printers, and adjusted at a final concentration of 8 µM. And a cartridge for use in thermal jet printers is filled with the DNA solution. The four types of probes 16 are arranged in the pattern shown in FIG. 5. Specifically, the probe No. 1 was arranged on the circumference with a radius of 14 mm, the probe No. 2 on the circumference with a radius of 13 mm, the probe No. 3 on the a circumference with a radius of 12 mm and the probe No. 4 on the-circumference with a radius of 11 mm in such a manner that all of them formed concentric circles (the probes are arranged in such a manner as to form concentric circles spaced at intervals of 1 mm in the order, No. 1, No. 2, No. 3 and No. 4 from the outside inward).

Then the substrate with the DNA solution placed thereon was left in a humid chamber for 30 minutes to react the substrate with DNA.

The thermal jet printer used was a remodeled type of thermal jet printer C-600, which is manufactured by Canon Inc. and capable of doing lithographic printing.

After the completion of the reaction, the substrate was washed with 1M NaCl/50 mM sodium phosphate buffer solution (pH 7.0), so as to wash the DNA solution away from the glass surface completely. Then the substrate was immersed in 2% bovine serum albumin aqueous solution, left for 2 hours, and subjected to blocking reaction. After the blocking reaction, the substrate was again washed with 1M NaCl/50 mM sodium phosphate buffer solution (pH 7.0), so as to obtain the substrate to which 4 types of DNAs were attached in the form of concentric circles.

(3) Synthesis of EOSIN-Labeled DNA

Amino-linked 18-mer DNA having a sequence complementary to that of the DNA attached to the substrate was synthesized by BEX at the request of the applicants of the present invention. As the amino group, used was a commonly used 5'-terminal-hexamethylene type amino linker.

5'-terminal-eosin-labeled DNA was obtained by reacting the amino-linked DNA with eosin-5-isothiocyanate, a protein-labeling dye manufactured by Funakoshi Co., Ltd. Labeling reaction was carried out by conventional procedure.

(4) Hybridization

Hybridization was carried out in the same manner as in the example 2 (4).

(5) Substrate Measurement

Measurements were made for the obtained substrate 1 with the measuring device used in the example 1. The rotation speed of the disk was set at 30000 rpm and the excitation light at 522 nm, like in the example 1.

The fluorescence spectrum at the portion to which probes 16 were attached was measured for each probe in order while allowing the disk to rotate and properly setting the positions of the excitation light illumination portion 13a and the objective lens 7. As a result, the fluorescence spectrum could be measured for 3 probes other than probe No. 4.

The measurements at 560 nm, where the intensity of fluorescence was the maximum, were as follows: 2300 for the probe No. 1, 1400 for the probe No. 2, and 1000 for the probe No. 3.

The results show that the more the base sequence of a sample is complementary to that of the probe, the more the fluorescence is intensive. And it is apparent from the results that the analysis of base sequences of nucleic acid can be performed with a fluorometric device in accordance with the present invention and a substrate on which more than one probes are arranged in the form of concentric circles.

The fluorometry in accordance with the present invention has the advantage of being capable of removing excitation light without a complicated device construction. It provides complete removal of excitation light, since its light detecting portion is placed in such a position that excitation light cannot approach.

The forms of providing samples for the fluorometric device in accordance with the present invention include a disk-shaped substrate. And in the use of such a disk-shaped substrate, measurements for the samples using more than one probes can be easily performed by arranging those probes on the substrate in the form of concentric circles with their centers at the rotational axis and with radii different from each other.

SEQUENCE LISTING

SEQ ID No.: 1
Length: 18
Type: Nucleic Acid
Strandedness: Single Stranded
Topology: Linear
Molecule type: Other Nucleic Acid, Synthetic DNA
D Sequence description:
ACTGGCCGTC GTTTTACA 18
SEQ ID No.: 2
Length: 18
Type: Nucleic Acid
Strandedness: Single Stranded
Topology: Linear
Molecule type: Other Nucleic Acid, Synthetic DNA
Sequence description:
ACTGGCCGTT GTTTTACA 18
SEQ ID No.: 3
Length: 18
Type: Nucleic Acid
Strandedness: Single Stranded
Topology: Linear
Molecule type: Other Nucleic Acid, Synthetic DNA
Sequence description:
ACTGGCCGCT TTTTTACA 18
SEQ ID No.: 4
Length: 18
Type: Nucleic Acid
Strandedness: Single Stranded
Topology: Linear
Molecule type: Other Nucleic Acid, Synthetic DNA
Sequence description:
ACTGGCATCT TGTTTACA 18
Sequence
ACTGGCCGCT TTTTTACA 18
SEQ. ID No.: 4
Length: 18
Type: Nucleic Acid
Strandedness: Single Strand
Topology: Linear
Molecule type: Other Nucleic Acid, Synthetic DNA
Sequence
ACTGGCATCT TGTTTACA 18

What is claimed is:

1. A method for measuring fluorescence emitted from samples on a measuring surface of a substrate by illuminating said samples with excitation light, characterized in that an excitation light illumination portion and a light detecting portion are moved independently of each other relative to said samples and are spaced apart in such a manner as to make it possible to prevent said excitation light from approaching said light detecting portion where measurements are made of said fluorescence, and the fluorescence emitted from the samples is measured while said excitation light illumination portion and said light detecting portion are moved relative to said samples after illuminating said samples with said excitation light.

2. The method according to claim 1, wherein said samples are liquid filled in cells formed on said substrate.

3. The method according to claim 1, wherein said samples are substances attached, adsorbed onto, or trapped in said substrate.

4. The method according to claim 1, wherein said samples are DNA.

5. The method according to claim 1, wherein said samples are protein.

6. The method according to claim 1, wherein said samples are peptide nucleic acid.

7. The method according to claim 1, wherein said samples are fixed on probes arranged on said substrate.

8. The method according to claim 7, wherein said probes are DNA.

9. The method according to claim 7, wherein said probes are protein.

10. The method according to claim 7, wherein said probes are peptide nucleic acid.

11. The method according to claim 1, wherein said spacing between said excitation light illumination portion and said light detecting portion is variable and the period from the illumination of excitation light to the detection of fluorescence is adjustable.

12. The method according to claim 1, wherein the speed of relative movement is variable and the period from the illumination of excitation light to the detection of fluorescence is adjustable by varying said speed.

13. The method according to claim 1, wherein said samples on said measuring surface of said substrate are arranged on more than one circle or on the arcs thereof which are concentric with the central axis of said substrate and are different in radius from each other, the samples at the same distance from the central axis having the same or similar attributes and forming a group which can be discriminated from the other groups of samples.

14. A fluorometric device comprising;
an excitation light illumination portion where samples on a measuring surface of a substrate are illuminated with excitation light;
a light detecting portion where measurements of the fluorescence emitted from the samples is performed; and
means for varying spacing between said excitation light illumination portion and said light detecting portion,
wherein said excitation light illumination portion and said light detecting portion are spaced apart in such a manner as to make it possible to prevent said excitation light from approaching said light detecting portion.

15. The fluorometric device according to claims 14, wherein the varying of the spacing between said excitation light illumination portion and said light detecting portion adjusts the period of time from the excitation light illumination to the light detection.

16. The fluorometric device according to claim 14, comprising means for varying a moving speed of the samples, with which the period of time from the excitation light illumination to the light detection is adjustable.

17. A method for measuring fluorescence emitted from samples on a measuring surface of a substrate by illuminating said samples with excitation light, characterized in that
an excitation light illumination portion and a light detecting portion are placed in such a manner as to make it possible to prevent said excitation light from approaching said light detecting portion where measurements are made of said fluoresence, and
the fluorescence emitted from the samples is measured while moving said excitation light illumination portion and said light detecting portion relative to the samples which are not moved.

* * * * *

UNITED STATES PATENT AND TRADEMARK OFFICE
CERTIFICATE OF CORRECTION

| | | |
|---|---|---|
| PATENT NO. | : 6,963,397 B2 | |
| APPLICATION NO. | : 09/764049 | |
| DATED | : November 8, 2005 | |
| INVENTOR(S) | : Tomohiro Suzuki et al. | |

It is certified that error appears in the above-identified patent and that said Letters Patent is hereby corrected as shown below:

COLUMN 4
Line 9, "thereby" should read --whereby--;
Line 66, "illumination portions" should read --illumination portion--; and
Line 67, "detecting portions" should read --detecting portion--.

COLUMN 5
Line 2, "one-different spots" should read --one different spot--;
Line 5, "spots" should read --spot--;
Line 32, "types" should read --type--;
Line 41, "probes" should read --probe--; and
Line 56, "left" should read --left to--.

COLUMN 6
Line 56, "a Measurements" should read --Measurements--.

COLUMN 7
Line 11, "left" should read --left to--; and
Line 37, "of the substrate was" should read --of the substrate were--.

COLUMN 8
Line 48, "a terminal" should read --terminal--; and
Line 65, "the-circumference" should read --the circumference--.

COLUMN 9
Line 53, "probes are" should read --probe is--.

UNITED STATES PATENT AND TRADEMARK OFFICE
CERTIFICATE OF CORRECTION

PATENT NO. : 6,963,397 B2
APPLICATION NO. : 09/764049
DATED : November 8, 2005
INVENTOR(S) : Tomohiro Suzuki et al.

It is certified that error appears in the above-identified patent and that said Letters Patent is hereby corrected as shown below:

COLUMN 10
Line 8, "D Sequence" should read --Sequence--; and

Lines 34-42, "ACTGGCCGCT TTTTTACA 18
SEQ. ID No.: 4
Length: 18
Type: Nucleic Acid
Strandedness: Single Strand
Topology: Linear
Molecule type: Other Nucleic Acid, Synthetic DNA
Sequence
ACTGGCATCT TGTTTACA 18" should be deleted.

COLUMN 12
Line 2, "is performed" should read --are performed--.

Signed and Sealed this

Twenty-fourth Day of October, 2006

JON W. DUDAS
*Director of the United States Patent and Trademark Office*